United States Patent [19]

Bilinsky et al.

[11] 4,128,097

[45] Dec. 5, 1978

[54] COMPRESSION DEVICE FOR TENNIS ELBOW

[76] Inventors: Michael C. Bilinsky, 515 Kelton Ave., Los Angeles, Calif. 90024; Robert L. Gold, 5967 E. Pacific Coast Hwy., Long Beach, Calif. 90803

[21] Appl. No.: 711,566

[22] Filed: Aug. 4, 1976

[51] Int. Cl.² .............................................. A61F 13/00
[52] U.S. Cl. .................................................. 128/165
[58] Field of Search .................... 128/165, 166, 80 R, 128/80 C, 80 H, 96, 77, 87 R

[56] References Cited

U.S. PATENT DOCUMENTS

| 2,641,761 | 6/1953 | Schultz | 128/80 C |
| 3,073,305 | 1/1963 | Biggs, Jr. et al. | 128/80 H X |
| 3,074,405 | 1/1963 | Duensing | 128/165 X |
| 3,194,233 | 7/1965 | Peckham | 128/165 X |
| 3,209,517 | 10/1965 | Hyman | 128/165 X |
| 3,703,171 | 11/1972 | Schiavitto | 128/80 C |
| 3,831,467 | 8/1974 | Moore | 128/80 C |
| 3,934,583 | 1/1976 | Hollingshead et al. | 128/165 |
| 3,970,081 | 7/1976 | Applegate, Jr. | 128/165 X |
| 3,970,083 | 7/1976 | Carrigan | 128/166 |

Primary Examiner—John D. Yasko
Attorney, Agent, or Firm—W. Edward Johansen

[57] ABSTRACT

The invention is a compression device for tennis elbow which compresses the common extensor muscle group of an individual so that he may continue to play tennis despite the presence of tennis elbow. The compression device includes an elastic member which is formed out of an elastic material and which has a tubular shape adapted to provide a compressive force on the common extensor muscle group of the individual. The elastic member has an outer surface and an inner surface. The elastic member also has a longitudinal slit which is fastened together by velcro fastening material. The compression device also includes a non-compressible member which is formed out of a non-rigid material and which is disposed on the inner surface of the elastic member. The non-compressible member is adapted to cover the common extensor muscle group. The compression device further includes a non-compressible pad which is formed out of a non-rigid material and which is disposed on the inner surface of the elastic member so that it covers the attachment area of the common extensor muscle group.

2 Claims, 6 Drawing Figures

COMPRESSION DEVICE FOR TENNIS ELBOW

BACKGROUND OF THE INVENTION

1. Field of the Invention

The present invention relates to a medical device for supporting musculotendinous units of an individual's extremities, and more particularly to a compression device for tennis elbow which not only enable the individual to continue to exercise without pain or further aggravation to an existing injury in his elbow, but which also prevents the occurrence of tennis elbow through a set of exercise procedures using the compression device.

2. Description of the Prior Art

The term tennis elbow may include many difficulties which may occur in and about the elbow; there are at least eleven specific elbow complaints which have been called tennis elbow. The primary symptom is a chronic inflammation of the attachment of the common extensor muscle group, which are the extensor carpi radialis brevis and extensor communis, to the lateral epicondyle as well as the attachment of the condylar origin of the radial collateral ligament. There are other muscle groups which originate from the elbow, specifically the olecraneum, including the acroneus which arises from the humerus, but which inserts into the extensor muscle group attachment area in the elbow. These muscle groups are also weak in their anatomical design.

It is believe that this chronic inflammation occurs because the mechanical construction of the elbow itself predisposes the individual to injury during movements of a tennis match. A prominent radial head creates a fulcrum with two leverage forces, one a long lever from the radial head just below the point of the elbow to the wrist where the muscles attach, and the other a short lever from the radial head to the point of the elbow, the lateral epicondyle. The long leverage force creates pressure against the attachment of the common extensor muscle mass, sujecting it to repetitive and chronic strain with the subsequent formation of non-elastic scar tissue. The scar tissue often tears again and tends to become reinflammed. The situation is compounded by the lack of lack of appropriate extensor muscle power to withstand the forces against it which is so characteristic of the occasional athlete who rarely trains for sports activity.

For the most part, the problem occurs because of an inherent weakness in the anatomical design or mechanical relationship of the muscles of the arm which subjects the elbow to increased stress within the area placing an inordinate strain on the tissues.

Treatment for tennis elbow has been primarily medical in nature ranging from localized injections of cortisone or surgery to simple rest.

It has been found that the pain of tennis elbow can be relieved and the injury itself prevented by placing pressure about the smaller muscles of the forearm. The pressure on the muscles serves to relieve the internal tension on the muscles by providing a force against which the muscles can push.

A bandage-like device called the Froimson Tennis Elbow support has been developed which can be wrapped about the forearm. Unfortunately, this device is difficult for the tennis player to put on unassisted and obtain the desired degree of tightness and pressure. In addition, the device, although coated on the side adjacent the skin with a foamed plastic, tends to slip off the arm during normal tennis pay, especially when the arm begins to sweat. Moreover, the device does not place a uniform pressure about the muscles unless wrapped carefully.

U.S. Pat. No. 3,877,426, entitled Muscular Support, issued to Robert P. Nirschl on April 15, 1975, teaches a support for bracing the musculotendinous units in the upper and lower extremities of humans. It is a flexible, arcuately shaped pad, especially adapted to be tightly wrapped about a muscle without slippage. The pad is constructed from a two layer laminate of cloth and foam rubber. The pad is easily tightened by a velcro fastener strip which is inserted through a fastening ring and reversedly drawn for attachment to itself.

U.S. Pat. No. 3,888,244, entitled Means for Supporting a Limb in Relaxed Position, issued to Steve Lebold on June 10, 1975, teaches a restraining member that is adapted to be positioned inside the elbow or knee joint and that has straps adapted to pass around the limb members above and below the joint to hold a pad in position while restraining the limb members in an angular position of rest. The pad is filled with soft resilient material such as sponge rubber, sponge polyvinyl polymer, cotton padding, felt or the like. Where necessary, the bottom surface of the pad may be reinforced with a semirigid member such as a flexible sheet of metal or plastic. When wearing the restraining member on his his elbow, an individual is not only unable to play tennis, but is also unable to exercise his extensor muscles in order to strengthen them. The individual is only able to rest his elbow.

U.S. Pat. No. 3,903,878, entitled Device for Supporting a Limb and Associated Extremity, issued to Donald C. Spann on Sept. 9, 1975, teaches a device for supporting a limb and associated extremity that is formed from a block of polyurethane foam, which is both air-permeable and resilient, and that has a polygonal cross-section and an groove extending along its entire length thereby providing a cradle for the limb. The block is secured about the limb by velcro fastening strips. This device is not for resting the elbow joint, but is described because it is formed out of polyurethane foam and has velcro fastening strips.

U.S. Pat. No. 3,892,239, entitled Quinohydrothermic Body Covering Element, issued to Jose Ma Masso Remiro on July 1, 1975, teaches a body covering element that includes a thin layer of rubber, which is essentially laminar in construction and which has a thickness progressively decreasing in one direction of the covering. The layer of rubber is non-porous, highly elastic and intimately associated with another layer of knitted fabric which covers one of its surfaces and which has a crenelated cross-section. The thin layer of rubber may be optionally covered on its other surface with a second layer of knitted fabric. One of the specific shapes that the body covering element may take is that of a tube which is narrower at one end than at the other, progressively changing in cross-section and dimension so that it becomes adapted to the part of the body to be covered. It can be used in athletic events to prevent twistings, sprains, torn ligaments and the like since the body covering element increases the resistance of the skeleton supporting, i.e. muscles and ligaments. Furthermore it potentializes the muscular contractibility and the elasticity of the ligaments thereby enhancing a better recovery after strechings.

SUMMARY OF THE INVENTION

In view of the foregoing factors and conditions characteristic of the prior art it is a primary object of the present invention to provide a compression device for tennis elbow which anchors the muscles of the common extensor group below their attachment points in order to reduce tension at their attachement points.

It is another object of the present invention to provide a compression device for tennis elbow which compresses the muscles of the common extensor group from their attachment points to where they intersect the wrist so that the muscle is restrained and relatively more compressed than the blood vessels and arteries.

It is also another object of the present invention to provide a compression device for tennis elbow which will prevent venous engorgement and will promote lymphatic drainage.

It is still another object of the present invention to provide a compression device for tennis elbow which enables an individual to exercise the muscles of the common extensor group so that they build up in strength and bulk and become an effective muscle group.

It is yet another object of the present invention to provide a compression device for tennis elbow which can be wrapped around the forearm and the elbow joint with substantially uniform pressure without the assistance from a second individual.

It is yet still another object of the present invention to provide a compression device for tennis elbow which resists slippage from its placement during vigorous athletic motion such as that which occurs during a game of tennis.

It is still yet another object of the present invention to provide a compression device for tennis elbow which is both preventive and therapeutic in nature.

In accordance with an embodiment of the present invention a compression device for tennis elbow which compresses the common extensor muscle group of an individual so that he may continue to play tennis despite the presence of tennis elbow has been described. The compression device includes an elastic member which is formed out of an elastic material and which has a tubular shape adapted to provide a compressive force on the common extensor muscle group of the individual. The elastic member has an outer surface and an inner surface. The elastic member also has a longitudinal slit which is fastened together by velcro fastening material. The compression device also includes a non-compressible member which is formed out of a non-rigid material and which is disposed on the inner surface of the elastic member. The non-compressible member is adapted to cover the common extensor muscle group. The compression device further includes a non-compressible pad which is formed out of a non-rigid material and which is disposed on the inner surface of the elastic member so that it covers the attachment area of the common extensor muscle group.

The features of the present invention which are believed to be novel are set forth with particularity in the appended claims.

Other objects and many of the attendant advantages of this invention will be more readily appreciated as the same becomes better understood by reference to the following detailed description and considered in connection with the accompanying drawing in which like reference symbols designate like parts throughout the figures.

DESCRIPTION OF THE PREFERRED EMBODIMENT

Figure 1:
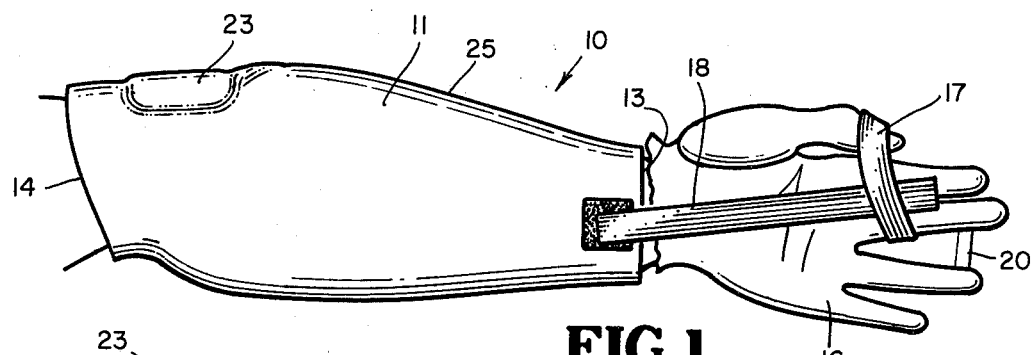
FIG. 1 is a perspective drawing of a compression device for tennis elbow, which is constructed in accordance with the principles of the present invention, that is placed on the forearm of an individual and that also covers his elbow and part of his upper arm.
Figure 2:
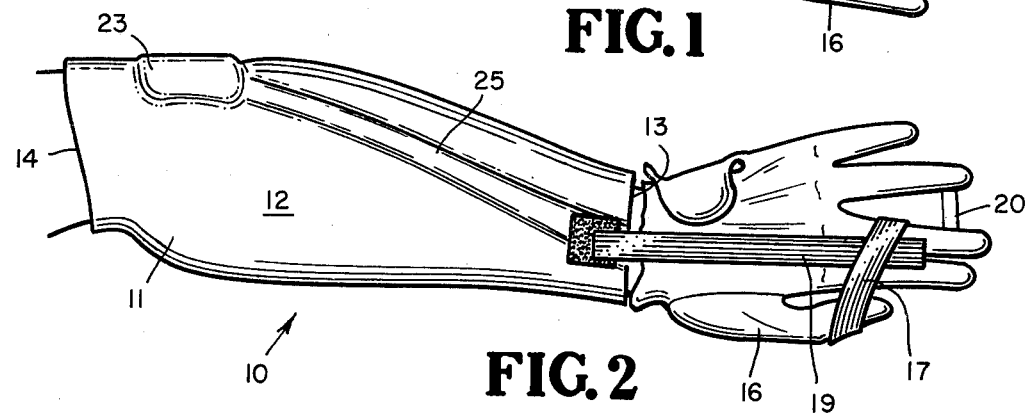
FIG. 2 is a plan view of a glove, whose top side is shown in FIG. 1, showing the bottom side of the glove.

The present invention is a compression device for an athletic injury. It can best be understood by reference to a description and a drawing of its preferred embodiment. Referring to FIG. 1, the preferred embodiment is a compression device for tennis elbow which includes an elastic member 11 which is tubular in shape and adapted to provide a compressive force on the common extensor muscle group of an individual. The elastic member 11 has an outer surface 12. It also has a longitudinal slit extending from end 13 to the other end 14 and is fastened together by a pair of velcro fastening strips 15. The compression device 10 for tennis elbow also includes a glove 16, which has a compartment for the thumb and four separate compartments for the fingers. The compartments for the thumb and first two fingers are bound together by a non-elastic, flexible material 17 and anchored to the outer surface 12 also by non-elastic, flexible material 18. Referring briefly to FIG. 2, the other side of the glove 16 is shown to have the compartments for the thumb and first two fingers anchored to the outer surface 12 by a non-elastic, flexible material 19. FIG. 2 further shows that the compartments for the second finger and the third finger are joined together by an elastic material 20.

Figure 3:
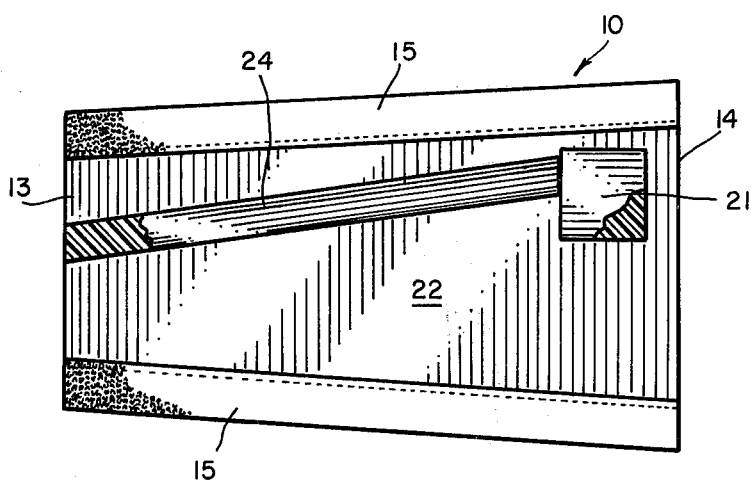
FIG. 3 is a plan view of the compression device of FIG. 1 before it is placed on the forearm of the individual.

Referring now to FIG. 3 in conjunction with FIG. 1, the compression device 10 for tennis elbow also includes a non-compressible member 21 formed out of a non-rigid material and adapted to cover the common extensor muscle group of the individual. The elastic member 11 has an inner surface 22 on which the non-compressible member 21 is disposed. The non-compressible member 21, when the compression device 10 is on the forearm, creates a bulge 23 which can be seen on the outer surface 12 of the elastic member 11. The compression device 10 for tennis elbow further includes a non-compressible pad 24 formed out of a non-rigid material and disposed on the inner surface 22 of the elastic member 11. The non-compressible pad 24 is adapted to cover the attachment area of the common extensor muscle group. The non-compressible pad 24, when the compression device 10 is on the forearm, also creates a bulge 25 which can be seen on the outer surface 12 of the elastic member 11.

Figure 4:
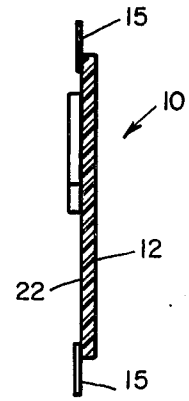
FIG. 4 is a side elevational view of the compression device of FIG. 3 which shows both a non-compressible pad and a non-compressible member disposed on the inner surface of the compression device.

Referring FIG. 4 in conjunction with FIG. 3, it can be seen that the velcro fastening strips 15 are sewn to the inner surface 22 of the elastic member 11 along the edges formed by the longitudinal slit. The non-compressible pad 24 and the non-compressible member 21 are also shown and are both formed from a moldable plastic material in the preferred embodiment. Other embodiments of the present invention have the non-compressible pad 24 and the non-compressible member 21 formed from such materials as a hard rubber, polyvinyl, cork, a packet of beads, aluminum, steel, and any other suitable splinting material including wood.

Figure 5:
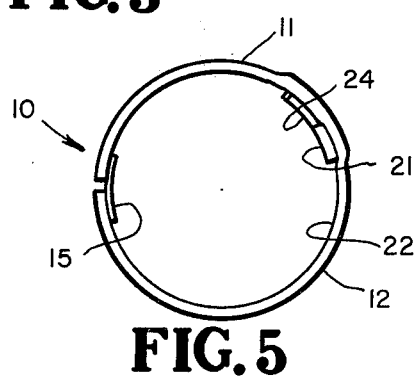
FIG. 5 is a side elevational view of the compression device of FIG. 1 which shows the compression device having a longitudinal slit joined together by velcro fastening strips.

FIG. 5 shows the elastic member 11 disposed about the forearm of an individual in a cross-sectional view. The pair of velcro fastening strips 15 are coupled together. Both the non-compressible member 21 and the non-compressible pad 24, and the bulges 23 and 25 caused by them, are shown in this view. The elastic member 11 is formed from a neoprene rubber and has a thickness which is generally in the range of one-sixteenth (1/16) of an inch to one-half (½) of an inch. In the preferred embodiment of the compression device 10 the elastic member has a thickness in the range of one-eighth (⅛) of an inch to three-sixteenths (3/16) of an inch in order to insure sufficient flexibility to play tennis. The elastic member 11 may be formed out of any combination of materials which can produce a compressive force such as leather in combination with an elastic material, canvas in combination with an elastic material and polyvinyl in combination with an elastic material.

The compression device 10 for tennis elbow is used to exercise the common extensor muscle group, the attachments to the olecraneum and the acroneus. It does this by anchoring the thumb and the first two finger and binding the common extensor muscle group, all the attachments to the olecraneum and the the acroneus so that these muscles may be exercise under compression. Furthermore, the elastic member 11 provide a compressive force of a lower magnitude than that force binding the muscles on the lymphatic and venous systems so that no pooling of their fluids occurs. The individual exercise these muscles by alternatingly separating his third and fourth fingers from the first and second fingers and bringing them back together again. This causes isometric contraction of the muscles and builds the muscles in size, strength and effect.

When the glove 16 is removed from the compression device for tennis elbow 10, it may be used to play tennis while the individual is suffering from tennis elbow. The compression device 10 binds the common extensor muscle group, all the attachments to the olecraneum and the acroneus so that the individual can continue to play tennis without pain or further aggravation to his injured elbow.

Figure 6:
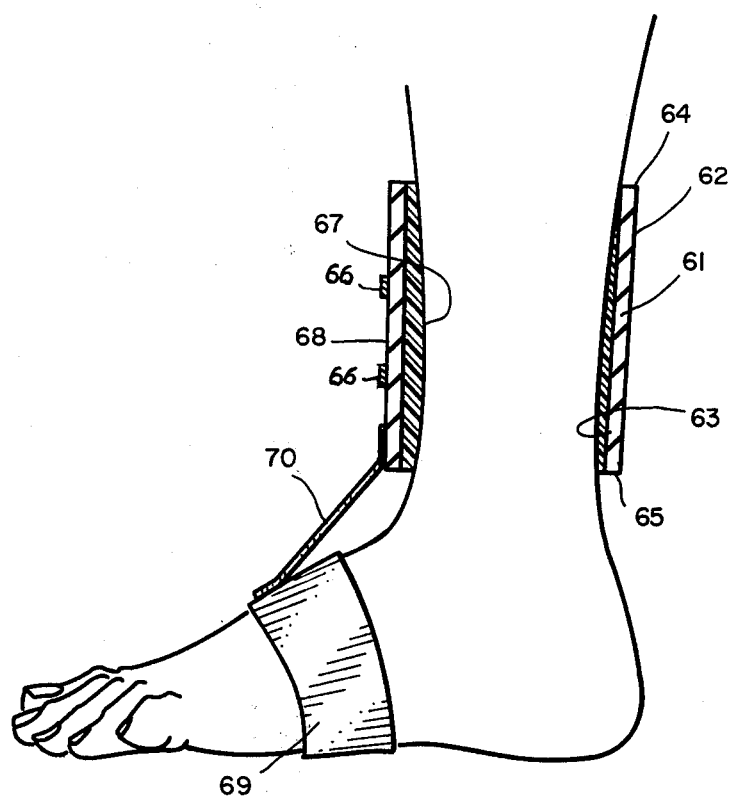
FIG. 6 is a cross-sectional view of a compression device for shin splints that is placed on the tibia. The compression device for shin splints is also constructed in accordance with the principles of the present invention.

A second embodiment of the present invention is a compression device 60 for shin splints and is shown in FIG. 6 as a longitudinal cross-sectional view. The compression device 60 includes an elastic member 61 which is tubular in shape and adapted to provide a compressive force on the anterior tibial tendon and muscle of an individual. The elastic member 61 has an outer surface 62 and an inner surface 63. It also has a longitudinal slit extending from one end 64 to the other end 65 and is fastened together by a pair of velcro fastening strips 66. The compression device 60 also includes a non-compressible member 67 formed out of a non-rigid material and adapted to cover the anterior tibial tendon and muscle of the individual. The non-compressible member 67 is disposed on the inner surface 63 of the elastic member 61 and creates a bulge 68 on the outer surface 62 of the elastic member 61, when the compression device 60 is on the tibia.

The compression device 60 further includes a spat 69, which is adapted to support the foot of an individual near the region of the matatarsals, and an elastic member 70, which is coupled to the outer surface 62 of the elastic member 61 and to the spat 69 in order to produce a plantarflexory motion causing activation of the anterior tibial muscle.

The compression device 60 for shin splints is used to exercise the anterior tibial muscle. It does this by binding the anterior tibial muscle so that this muscle may be exercised under compression. Further, the elastic member 61 provides a compressive force of a lower magnitude than the force binding the muscle on the lymphatic and venous systems so that no pooling of their fluids occurs. The individual is therefore able to run without pain or further aggravation to the injury in his shins.

From the foregoing it can be seen that a compression device for athletic injuries has been described. The compression device includes an elastic member that compresses a particular group of muscles and a non-compressible member that is adapted to cover the particular group of muscles.

It should be noted that the schematic drawings of the compression device are not drawn to scale and the distances of and between figures are not to be considered significant.

Accordingly, it is intended that the foregoing disclosure and showing made in the drawings shall be considered only as illustrations of the principles of the present invention.

What is claimed is:

1. A compression device for compressing the common extensor muscle group of an individual so that he may exercise this muscle group of an individual so that he may exercise this muscle group in order to prevent the occurrence of tennis elbow, said compression device comprising:
  a. An elastic member formed out of an elastic material and having a tubular shape adapted to provide a compressive force on the group of muscles and tendons of the individual, said elastic member having an inner surface and an outer surface; and
  b. a non-compressible member formed out of a non-rigid material and disposed on said inner surface of said elastic member, said non-compressible member being adapted to cover the group of muscles and tendons to be protected;
  c. a non-compressible pad formed out of a non-rigid material and disposed on said inner surface of said elastic member so that it covers the attachment area of the common extensor muscle group;
  d. a glove having compartments for a thumb and four fingers, with said compartments for the thumb and first two fingers being fastened together; and
  e. means for anchoring the thumb and first two fingers so that they cannot move, mechanically coupled to said glove and to said outer surface of said elastic member.

2. A compression device for compressing the common extensor muscle group of an individual so that he may exercise this muscle group in order to prevent the occurrence of tennis elbow, according to claim 1, wherein said compression device also comprises an elastic member coupling said compartments for the second and third fingers together.

* * * * *